United States Patent [19]

Ranson et al.

[11] Patent Number: 5,708,272
[45] Date of Patent: Jan. 13, 1998

[54] APPARATUS FOR DETERMINING A PARAMETER OF A SUBSTANCE, ESPECIALLY A HYDROCARBON

[75] Inventors: Aaron Ranson, San Antonio; Pedro Felipe Tovar, Los Teques; Adriano Filadelfo Parisi, Los Nuevos Teques, all of Venezuela

[73] Assignee: Intevep, S.A., Caracas, Venezuela

[21] Appl. No.: 642,579

[22] Filed: May 3, 1996

[51] Int. Cl.⁶ .................. G01N 21/35; G01N 21/05
[52] U.S. Cl. .................. 250/339.12; 356/246
[58] Field of Search .................. 250/339.12; 356/246

[56] References Cited

U.S. PATENT DOCUMENTS 5,412,581  5/1995  Tackett ............ 364/498

FOREIGN PATENT DOCUMENTS 3336164  5/1985  Germany ............ 356/246

Primary Examiner—Constantine Hannaher
Attorney, Agent, or Firm—Bachman & LaPointe,P.C.

[57] ABSTRACT

An apparatus for determining a parameter of substance includes a cell defining an inner space, an inlet associated with the cell for introducing a sample of the substance to the inner space, an outlet associated with the cell for removing the sample from the inner space, an optic couple for passing NIR radiation through the sample in the inner space along an optic path so as to provide an NIR spectrum indicative of a parameter of the sample, the optic couple defining the optic path, and structure for directing flow in the inner space, whereby vortices within the inner space are inhibited and the NIR spectrum is rapidly provided upon introduction of the sample to the inner space.

22 Claims, 2 Drawing Sheets

APPARATUS FOR DETERMINING A PARAMETER OF A SUBSTANCE, ESPECIALLY A HYDROCARBON

BACKGROUND OF THE INVENTION

The invention relates to a system and apparatus for determining a parameter of a substance, especially a hydrocarbon, using NIR spectroscopy and a trained neural network.

Numerous industrial processes require precise supervision of parameters of certain types of materials. For example, increasingly stringent environmental protection laws demand precise methods for quality control of fuels during the mixing process of same. Existing methods for monitoring parameters of hydrocarbon do not provide sufficiently precise methods of measurement, and further do not provide substantially on-line results, thereby preventing the desired precision with respect to quality control and the like.

It is apparent that the need remains for an accurate and reliable apparatus for determining parameters of substances such as hydrocarbons in a substantially on-line manner especially with respect to compositions having parameters which are "NIR-correlationable", that is, which can be determined from an NIR spectrum.

It is therefore the primary object of the present invention to provide an apparatus for accurately determining a parameter of a sample, especially of a hydrocarbon material.

It is a further object of the present invention to provide a compact apparatus for determining the desired parameter in a substantially on-line manner.

It is a still further object of the present invention to provide an apparatus which is suitable for use in determining parameters of a wide variety of materials.

It is another object of the present invention to provide an apparatus wherein the desired parameter is determined with very fast response times.

It is still another object of the present invention to provide an apparatus wherein results are reproducible and repeatable within requirements such as those fixed by ASTM standards.

Other objects and advantages of the present invention will appear hereinbelow.

SUMMARY OF THE INVENTION

In accordance with the present invention, the foregoing objects and advantages are readily attained.

According to the invention, an apparatus is provided for determining one or more parameters of a substance such as a hydrocarbon, wherein the apparatus comprises a cell defining an inner space, inlet means associated with said cell for introducing a sample of said substance to said inner space, outlet means associated with said cell for removing said sample from said inner space, optic means for passing NIR radiation through said sample in said inner space along an optic path so as to provide an NIR spectrum indicative of a parameter of said sample, said optic means defining said optic path, and means for directing flow in said inner space, whereby vortices within said inner space are inhibited and said NIR spectrum is rapidly provided upon introduction of said sample to said inner space.

In further accordance with the invention, the cell preferably defines an upper area above said optic path and a lower area below said optic path, and said means for directing flow further comprises means for guiding bubbles from said sample to said upper area, and for guiding sediment from said sample to said lower area.

Still further according to the invention, the apparatus preferably further includes an analyzer associated with the cell for analyzing the NIR spectrum so as to determine the desired parameter. In accordance with a preferred embodiment of the invention, the analyzer means comprises a neural network trained to quantitatively correlate the NIR spectrum with the desired parameter.

BRIEF DESCRIPTION OF THE DRAWINGS

A detailed description of preferred embodiments of the invention follows, with reference to the attached drawings wherein.

DETAILED DESCRIPTION

The invention relates to an apparatus for determining a parameter of a substance or composition, particularly for determining a parameter of a fluid substance having Near Infra-Red (NIR) correlatable properties.

Numerous processes including refining of petrochemicals and processes in other industrial fields such as pharmaceuticals, food, cosmetics, beverages, paints and the like require compliance with stringent laws demanding precise quality control and monitoring of various parameters of the fluids, ingredients, end products and the like associated with such processes.

In the refining of petrochemicals, for example during the production of fuel, many of the fluids involved in the process have properties or parameters which can be determined through correlation to an NIR spectrum. Examples of such parameters of a hydrocarbon include RON, MON, RVP, oxygen content, aromatic content, olefin content, benzene content, D-86 and the like. In accordance with the invention, a system and apparatus are provided for determining a desired parameter of a substance such as a hydrocarbon by passing NIR radiation through a sample of the substance of interest, and analyzing the resulting NIR spectrum so as to determine the desired parameter.

In accordance with the present invention, a system and apparatus are provided for obtaining an NIR analysis of a sample of a desired substance for analysis and determination of the desired parameter.

Figure 1:
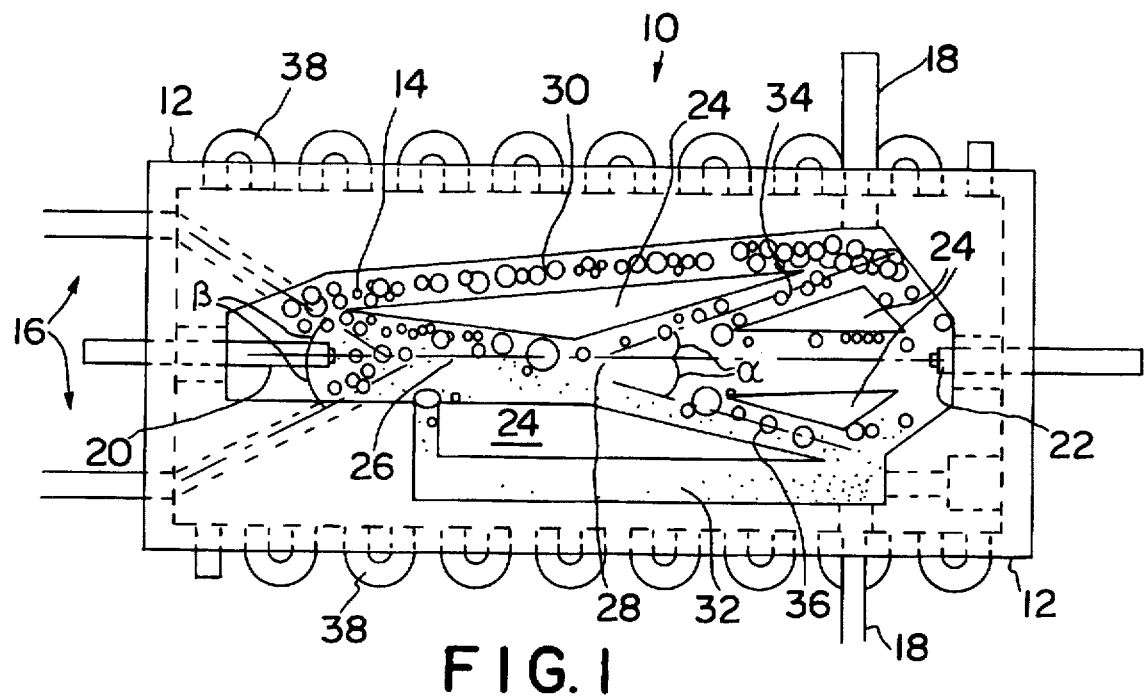
FIG. 1 is a side schematic view of a test cell in accordance with the invention.

FIG. 1 illustrates an apparatus for obtaining an NIR spectrum in accordance with the invention. As shown in the drawing, a cell or chamber 10 is provided according to the invention and connected to a source of the material to be analyzed so that a sample of the material can be introduced into chamber 10 for analysis in accordance with the invention.

As shown in FIG. 1, chamber 10 includes a wall member 12 defining an inner space 14, one or more inlets 16 for introduction of sample according to the invention, one or more outlets 18 for removing sample from inner space 14, an optic couple or pair such as an optic source 20 and an optic receiver 22, and flow directing structure such as contoured elements 24 for desirably and advantageously directing flow of fluid sample material within chamber 10 so as to inhibit vortex flow and encourage separation or removal of bubbles and sediment material from an optic path 26 within inner space 14 of chamber 10, thereby providing for rapid analysis of the sample within chamber 10 as desired in accordance with the invention.

Chamber 10 is preferably a substantially closed chamber or cell having wall members 12 made, for example, of stainless steel and preferably capable of sustaining very high pressures such as about 300 psi to about 800 psi.

Inlets 16 may suitably be provided as one or more inlet pipes, preferably arranged so as to introduce sample fluid material into inner space 14 of chamber 10 at an angle to optic path 26 of between about 30° to about 60°, most preferably about 45°.

Outlets 18 may suitably be provided as an upper and lower outlet pipe as shown in the drawings, for removal of fluid sample as well as separated bubbles and sediment. Of course, although a particular embodiment of outlets 18 and inlets 16 as described above are shown in FIG. 1, numerous alternative configurations of inlets 16 and outlets 18 could suitably be used within the scope of the present invention.

Still referring to FIG. 1, an optic couple or pair such as optic source 20 and optic receiver 22 are preferably positioned with respect to chamber 10 so as to direct NIR radiation along optic path 26 from source 20 to receiver 22. In accordance with the invention, an NIR spectrum is created due to passage of NIR radiation through sample material along optic path 26, and the NIR spectrum is received at optic receiver 22 and can be analyzed as will be discussed below so as to determine certain parameters of the sample or fluid within inner space 14 as desired in accordance with the invention. Obtaining an NIR spectrum from the sample contained within inner space 14 can be accomplished through numerous means well known to a person of ordinary skill in the art, for example using collimators at one or both of optic source 20 and optic receiver 22, and optic fiber for carrying the desired signal to a suitable analyzer.

As set forth above, contoured elements 24 are positioned in accordance with the invention within inner space 14 so as to advantageously avoid turbulent flow of sample material within chamber 10 by inhibiting and substantially reducing vortices caused by introduction of fluid through inlets 16 into inner space 14. Further, contoured elements 24 serve to enhance the separation of bubbles and sediment from fluid introduced to inner space 14 so as to provide a more effective and "noise-free" signal from a sample in optic path 26 for measurement in accordance with the invention.

As shown in FIG. 1, inner space 14 is preferably divided into a number of zones, specifically, a measurement zone 28 through which optic path 26 traverses and upper or bubble collecting zone 30, and a lower or sediment collecting zone 32. In accordance with the invention, a plurality of contoured elements 24 are preferably provided and arranged within inner space 14 so as to define an upper passage 34 and a lower passage 36 which branch off from measurement zone 28 and lead to upper zone 30 and lower zone 32 respectively as shown. In accordance with the invention, upper passage 34 and lower passage 36 preferably have a central axis which is arranged at an angle ($\alpha$) with respect to optic path 26, and angle ($\alpha$) is preferably between about 30° to about 35°. This advantageously serves to guide bubbles in upper passage 34 and sediment in lower passage 36 toward upper zone 30 and lower zone 32 respectively without inducing additional turbulence or vertices to flow within inner space 14. Thus, in accordance with the invention, contoured elements 24 advantageously serve to enhance the removal of bubbles and sediment from measurement zone 28, and further serve to induce a less turbulent flow within measurement zone 28 so that measurements can be taken using optic source 20 and optic receiver 22 in a more effective and reliable manner, and after a shorter settling period for measurements taken in a non-flowing condition.

In accordance with an embodiment of the invention, inlets 16 are selectively used for introducing a cleaning material to inner space 14 within chamber 10 so as to expose optic source 20 and optic receiver 22 to cleaning material as desired. In accordance with the invention, it has been found that enhanced cleaning is provided by positioning inlets 16 through which cleaning material is introduced at an angle ($\beta$) with respect to optic path 26 of between about 45° to about 65°, preferably between about 55° to about 60°. The introduction of cleaning material through inlet 16 in accordance with the invention will be further discussed below.

In accordance with a further alternative embodiment of the invention, chamber 10 is also preferably provided with a heat exchanger member 38 which may suitably comprise a conduit or other flow member arranged relative to chamber 10, for example in a zig-zag or parallel pipe pattern as shown in the drawings. Advantageously, and as will be further discussed below, when a sample is shut within chamber 10 for measurement, flow of material can be redirected to heat exchanger 38 so as to take advantage of heat exchange possibilities from such flow, and further to avoid back-up in a system to which chamber 10 is attached during measurement of a sample within inner space 14.

Figure 2:
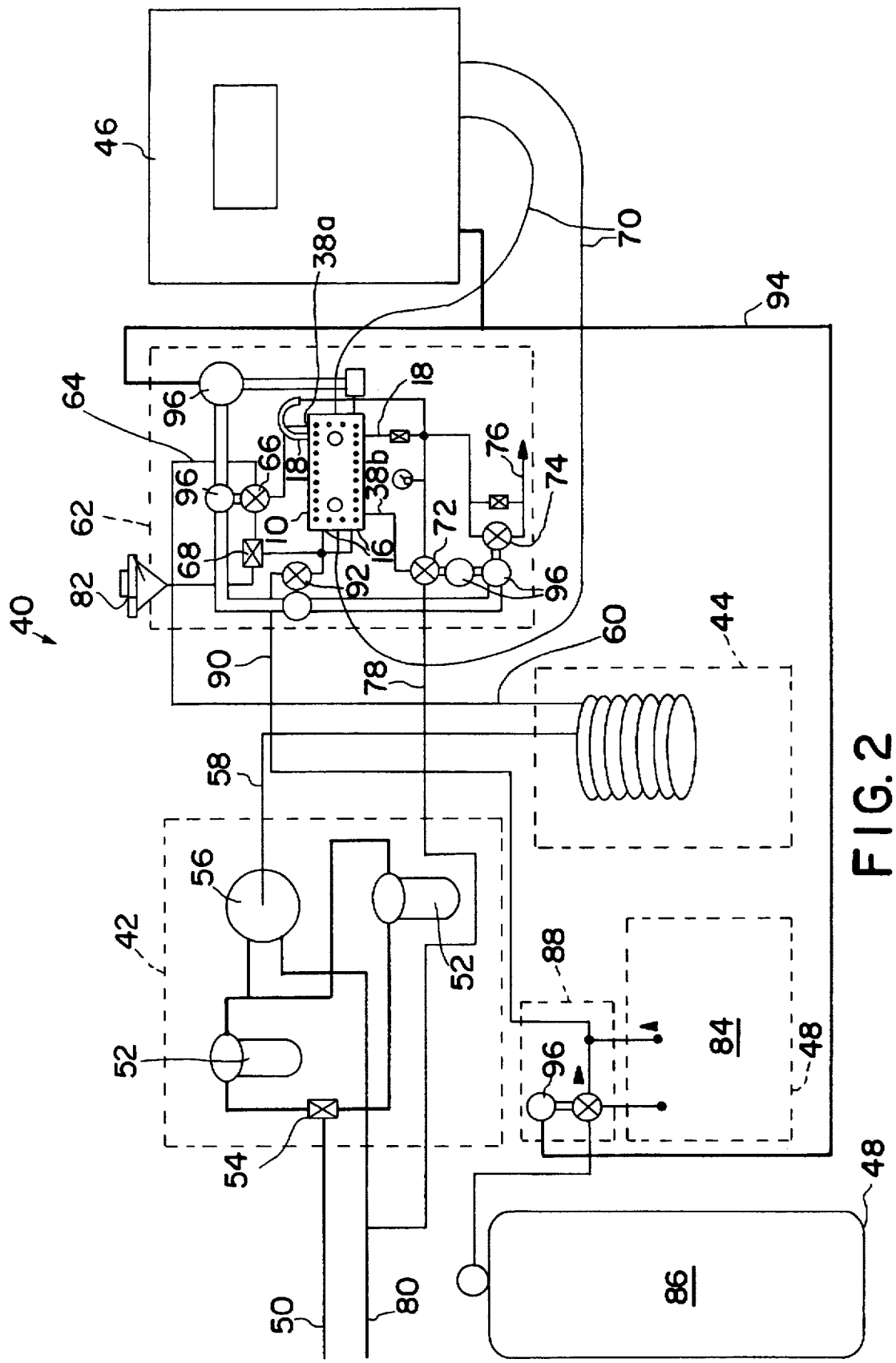
FIG. 2 is a schematic illustration of a system in accordance with the invention.

Referring now to FIG. 2, a system is illustrated incorporating chamber 10 in accordance with the invention for obtaining samples of fluid to be measured from a source of material such as a hydrocarbon production pipeline or any other means for conveying such material, and for transporting and conditioning the sample so as to introduce the sample for analysis to chamber 10 in accordance with the invention with contaminants such as water and particulate matter removed, and at a desired temperature.

As shown in FIG. 2, in addition to chamber 10, system 40 in accordance with the invention preferably includes a filtration unit 42, a conditioning unit 44, an analysis unit 46 for analyzing the NIR spectrum obtained from a particular sample, and optionally a source of cleaning materials 48 for cleaning the inner space 14 of chamber 10, especially for cleaning optic source 20 and optic receiver 22 as desired in accordance with the invention.

Filtration unit 42 according to the invention preferably includes a line 50 connected to a source of material to be analyzed. Line 50 preferably leads to a first filter system, preferably including two coalescent filters 52 connected in parallel to line 50. A valve member 54 is preferably positioned along line 50 for selectively directing flow to one or the other of filters 52 in accordance with the invention so that operation of system 40 need not be interrupted in order to clean or service one or the other of coalescent filters 52. Still further according to the invention, filtration unit 42 preferably includes a centrifugal filter 56 connected downstream from coalescent filters 52 and leading to a fluid outlet from filtration unit 42.

According to the invention, coalescent filters 52 advantageously serve to remove certain contaminants from a hydrocarbon to be measured, such as water and large particulate matter, while centrifugal filter 56 serves to remove smaller particles, thereby providing a filtered hydrocarbon material for measurement and analysis in accordance with the invention. Outlet 58 from filtration unit 42 preferably leads to conditioning unit 44 which will be discussed below.

Conditioning unit 44 preferably comprises means for adjusting the temperature of the fluid or other material introduced thereto to a suitable temperature for measurement in accordance with the invention. Preferably, conditioning unit 44 includes a coiled flow passage which may be immersed in a heated bath or other source of conditioning temperature, and may suitably serve to adjust the temperature of the fluid to be conditioned to a suitable temperature for conditioning prior to analysis. A suitable temperature depends upon the material to be tested, but a temperature of about 24.5° C. has been found to be suitable for hydrocarbons. Conditioning unit 44 has an outlet 60 for carrying conditioned material to chamber system 62 including chamber 10 for measurement and analysis in accordance with the invention.

Still referring to FIG. 2, chamber system 62 preferably includes a sample inlet line 64 connected to outlet 60 from conditioning unit 44 and leading to one or more valves 66, 68 for directing flow selectively to inlets 16 of chamber 10 or heat exchanger inlet 38a. Chamber system 62 as shown also includes heat exchanger outlet 38b and chamber outlets 18 as well as optic source 20 and optic receiver 22 connected to analysis unit 46 preferably through optic fibers 70 or the like.

Still referring to FIG. 2, heat exchanger outlet 38b as well as outlets 18 are connected to a series of valves 72, 74 which can be operated to direct flow from chamber 10 and/or heat exchanger 38 selectively to a drain line 76 or to a return line 78 leading to an overall system outlet 80 for returning or recycling the sample and/or fluid to the production line.

In accordance with the invention, analysis unit 46 is preferably a neural network device programmed and/or trained to correlate an NIR spectrum of a particular material with the desired parameter. In this regard, chamber system 62 preferably further includes a sample inlet 82 for use in introducing "known-composition" test samples into chamber 10 for use in training of the neural network of analysis unit 46 in accordance with the invention.

As set forth above, and in accordance with a preferred embodiment of the invention, system 40 also preferably includes cleaning materials units 48 for providing cleaning materials to inner space 14 of chamber 10 in accordance with the invention. As shown, cleaning material unit 48 may include a source 84 of solvent and a source 86 of nitrogen. As shown, solvent source 84 is preferably connected through a valve unit 88 to an inlet line 90 leading to a valve 92 for controlling flow into chamber 10. Nitrogen source 86 is also preferably connected to line 90 through valve unit 88. In accordance with the invention, and advantageously, when the optic couple of chamber 10 is to be cleaned, sample material is removed from chamber 10 and valve unit 88 and valve 92 are opened so as to initially introduce solvent to inner space 14. After a sufficient treatment with solvent, valve unit 88 is again operated so as to stop flow of solvent from solvent source 84, and introduce nitrogen from nitrogen source 86 to inner space 14 so as to dry components of the optic couple and other areas of inner space 14 and thereby prepare chamber 10 for subsequent measurement. Of course, a wide variety of solvents and alternatives to nitrogen could be used in accordance with the invention.

In further accordance with the invention, and still as shown in FIG. 2, analysis unit 46 may also be configured so as to control the various valves and valve units of system 40 in accordance with the invention through control line 94 and valve actuators 96 as desired in accordance with the invention.

In use, inlet line 50 is connected to a source of material such as hydrocarbon to be tested. Valve 54 is set to direct flow of hydrocarbon to one or the other of coalescent filters 52. Partially filtered sample travels from filter 52 to filter 56 for further removal of contaminants, and is then passed to conditioning unit 44 for proper adjustment of temperature. Filtered and conditioned material is then passed from conditioning unit 44 to chamber system 62 where valves 66, 68 are initially operated to introduce sample to inner space 14 of chamber 10 in accordance with the invention. Once inner space 14 is full, chamber 10 is closed, and valve 66 is operated so as to direct flow of material to heat exchanger inlet 38a in accordance with the invention. Analysis unit 46 is then operated so as to obtain a NIR spectrum from the optic couple and to thereby determine the desired parameter in accordance with the invention. Upon completion of the measurement, valves 66, 68 are again opened, as are the valves controlling outlets 18, so as to remove the sample from inner space 14 and prepare for the next measurement. Alternatively, if desired, valves 72, 74 can be operated so as to discharge fluid within inner space 14 to a drain 76.

When it is desired to clean chamber 10, hydrocarbon material is directed by valve 66 to heat exchanger inlet 38a, and solvent is directed from solvent source 84 through valve unit 88 to inlets 16 so as to remove materials which are deposited or otherwise accumulated on optic source 20 and optic receiver 22. After a suitable cleaning with solvent from solvent source 84, valve unit 88 is again operated so as to connect nitrogen source 86 to line 90 and thereby expose inner space 14, optic source 20 and optic receiver 22 to a flow of nitrogen for drying as desired in accordance with the invention. Upon completion of nitrogen flow, valve unit 88 is again operated so as to stop flow of nitrogen, and valves 66, 68 can be operated to again introduce a new sample of fluid or hydrocarbon to inner space 14 for testing in accordance with the invention.

Figure 3:
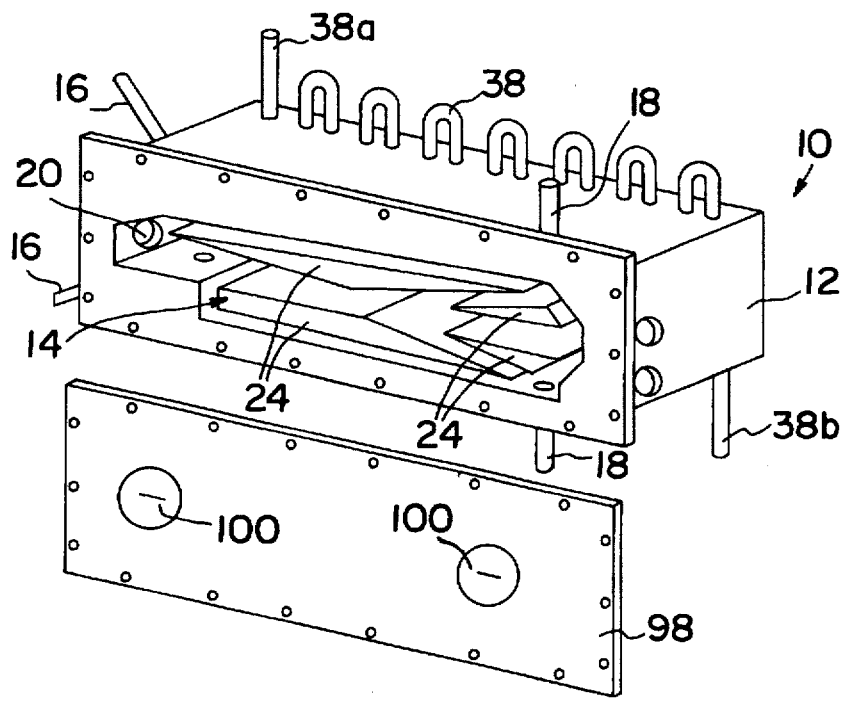
FIG. 3 is a partially exploded view of the test cell of FIG. 1.

Referring now to FIG. 3, a schematic and partially exploded view of chamber 10 according to the invention of FIG. 1 is shown. In accordance with the illustration of FIG. 3, it is readily apparent that chamber 10 in accordance with the invention may be provided with a removable face plate member 98 having removable plug members 100 which are useful in accordance with the invention to provide access to inner space 14 and contoured elements 24 as well as optic source 20 and optic receiver 22 for service, maintenance, cleaning and the like.

In accordance with the invention, it should be readily appreciated that a system and apparatus have been provided in accordance with the invention for advantageously determining parameters of a desired material wherein measurements are obtained in a reliable, efficient and rapid manner, and results so obtained are quantitative and therefore useful in stringent quality control procedures.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. An apparatus for determining a parameter of substance, comprising:

a cell defining an inner space;

inlet means associated with said cell for introducing a sample of said substance to said inner space;

outlet means associated with said cell for removing said sample from said inner space;

optic means for passing NIR radiation through said sample in said inner space along an optic path so as to provide an NIR spectrum indicative of a parameter of said sample, said optic means defining said optic path; and means for directing flow in said inner space, whereby vortices within said inner space are inhibited and said NIR spectrum is rapidly provided upon introduction of said sample to said inner space, said means for directing flow further comprises means for guiding bubbles from said sample into an upper area of said inner space above said optic path, and for guiding sediment from said sample to a lower area of said inner space below said optic path such that substantially all of the bubbles and sediment is diverted away from the optic path.

2. An apparatus according to claim 1, further comprising analyzer means associated with said cell for analyzing said NIR spectrum so as to determine said parameter.

3. An apparatus according to claim 2, wherein said analyzer means comprises a neural network trained to quantitatively correlate said NIR spectrum with said parameter.

4. An apparatus according to claim 1, wherein said optic means comprises an optic source for initiating said NIR radiation along said path, and an optic receiver for receiving said NIR spectrum from said path.

5. An apparatus according to claim 4, further comprising means associated with said cell for cleaning said optic source and said optic receiver.

6. An apparatus according to claim 5, wherein said means for cleaning comprises means for exposing said optic source and said optic receiver to a cleaning material.

7. An apparatus according to claim 6, wherein said means for exposing comprises a solvent inlet for introducing a solvent to said inner space, and a nitrogen inlet for introducing nitrogen to said inner space, whereby said optic source and said optic receiver can be sequentially exposed to said solvent for cleaning and to said nitrogen for drying.

8. An apparatus according to claim 1, wherein said means for directing comprises at least one contoured member positioned within said inner space to direct flow of said sample in said inner space.

9. An apparatus according to claim 8, wherein said at least one contoured member defines a first passage having a first axis angled generally upwardly with respect to said optic path, and a second passage having a second axis angled generally downwardly with respect to said optic path.

10. An apparatus according to claim 9, wherein said cell defines an upper area above said optic path and a lower area below said optic path, and wherein said first passage leads to said upper area and said second passage leads to said lower area.

11. An apparatus according to claim 9, wherein said optic path has a longitudinal axis and wherein said first axis and said second axis are arranged at angles ($\alpha$) respectively with respect to said longitudinal axis of between about 30° to about 60°.

12. An apparatus according to claim 11, wherein said inlet means comprises means for introducing said sample in a flow direction at an angle ($\beta$) with respect to said longitudinal axis of between about 45° to about 65°.

13. An apparatus according to claim 1, further comprising heat exchanger means associated with said cell and means for selectively directing said sample to said inlet means and said heat exchanger means.

14. A system for obtaining a parameter of a substance, comprising:

a cell defining an inner space;

inlet means associated with said cell for introducing a sample of said substance to said inner space;

outlet means associated with said cell for removing said sample from said inner space;

optic means for passing NIR radiation through said sample in said inner space along an optic path so as to provide an NIR spectrum indicative of a parameter of said sample, said optic means defining said optic path;

means for directing flow in said inner space, whereby vortices within said inner space are inhibited, said means for directing flow further comprises means for guiding bubbles from said sample into an upper area of said inner space above said optic path, and for guiding sediment from said sample to a lower area of said inner space below said optic path such that substantially all of the bubbles and sediment is diverted away from the optic path; and means for providing said sample of said substance to said inlet means.

15. A system according to claim 14, wherein said means for providing comprises a source of said sample, and means for filtering said sample so as to substantially remove water and particulate matter from said sample.

16. A system according to claim 15, wherein said means for providing further comprises conditioning means for providing said sample at a preselected temperature.

17. A system according to claim 14, further comprising analyzer means associated with said cell for analyzing said NIR spectrum so as to determine said parameter.

18. An apparatus according to claim 17, wherein said analyzer means comprises a neural network trained to quantitatively correlate said NIR spectrum with said parameter.

19. A system according to claim 14, further comprising means for providing a cleaning material for cleaning said optic means, and means for selectively connecting said means for providing said sample and said means for providing said cleaning material to said inlet means.

20. A system according to claim 19, wherein said means for selectively connecting has a first position wherein said means for providing said sample is connected to said inlet means, and a second position wherein said means for providing said cleaning material is connected to said inlet means and said sample is recycled to said means for providing said sample.

21. A system according to claim 20, further comprising heat exchanger means associated with said cell, and wherein said sample is recycled through said heat exchanger means when said means for selectively connecting is in said second position.

22. An apparatus for determining a parameter of substance, comprising:

a cell defining an inner space;

inlet means associated with said cell for introducing a sample of said substance to said inner space;

outlet means associated with said cell for removing said sample from said inner space;

optic means for passing NIR radiation through said sample in said inner space along an optic path so as to provide an NIR spectrum indicative of a parameter of said sample, said optic means defining said optic path;

means for directing flow in said inner space, whereby vortices within said inner space are inhibited and said NIR spectrum is rapidly provided upon introduction of said sample to said inner space; and heat exchanger means associated with said cell and directing means for selectively directing said sample to said inlet means and said heat exchanger means.

* * * * *